United States Patent [19]
Berg et al.

[11] Patent Number: 5,680,873
[45] Date of Patent: Oct. 28, 1997

[54] BRAIDLESS GUIDE CATHETER

[75] Inventors: Todd A. Berg, Lino Lakes; Brian Scovil, New Hope; Jason A. Galdonik, Brooklyn Park; Thomas J. Bachinski, Lakeville, all of Minn.

[73] Assignee: SciMed Life Systems, Inc., Maple Grove, Minn.

[21] Appl. No.: 398,214

[22] Filed: Mar. 2, 1995

[51] Int. Cl.⁶ ............................................. A61B 5/00
[52] U.S. Cl. .................. 128/772; 128/657; 128/658; 604/95; 604/96; 604/280
[58] Field of Search ............................ 128/772, 657, 128/658; 604/95, 280, 161; 606/159

[56] References Cited

U.S. PATENT DOCUMENTS

| | | | |
|---|---|---|---|
| 3,890,977 | 6/1975 | Wilson | 128/418 |
| 4,563,181 | 1/1986 | Wijayarathna et al. | 604/280 |
| 4,738,666 | 4/1988 | Fuqua | 604/280 |
| 4,759,748 | 7/1988 | Reed | 604/95 |
| 4,834,709 | 5/1989 | Banning et al. | 604/170 |
| 4,863,442 | 9/1989 | DeMello et al. | 604/282 |
| 4,904,431 | 2/1990 | O'Maleki | 264/103 |
| 4,923,061 | 5/1990 | Trombley, III | 206/364 |
| 4,935,017 | 6/1990 | Sylvanowicz | 604/280 |
| 5,061,257 | 10/1991 | Martinez et al. | 604/282 |
| 5,078,702 | 1/1992 | Pomeranz | 604/280 |
| 5,102,415 | 4/1992 | Guenther et al. | 606/159 |
| 5,120,323 | 6/1992 | Shockey et al. | 604/282 |
| 5,171,232 | 12/1992 | Castillo et al. | 604/280 |
| 5,221,263 | 6/1993 | Sinko et al. | 604/161 |
| 5,234,407 | 8/1993 | Teirstein et al. | 604/53 |
| 5,267,982 | 12/1993 | Sylvanowicz | 604/281 |
| 5,290,229 | 3/1994 | Paskar | 604/95 |
| 5,306,263 | 4/1994 | Voda | 604/281 |
| 5,333,620 | 8/1994 | Moutatis et al. | 128/772 |
| 5,334,168 | 8/1994 | Hemmer | 604/281 |
| 5,334,169 | 8/1994 | Brown et al. | 604/282 |
| 5,335,410 | 8/1994 | Burnham | 29/452 |
| 5,383,923 | 1/1995 | Webster, Jr. | 607/125 |
| 5,389,090 | 2/1995 | Fischell et al. | 604/280 |

FOREIGN PATENT DOCUMENTS

| | | |
|---|---|---|
| 0 277 366 A1 | 8/1988 | European Pat. Off. |
| 0 339 799 B1 | 11/1989 | European Pat. Off. |
| 0 439 932 B1 | 8/1991 | European Pat. Off. |
| WO 93/08861 | 5/1993 | WIPO |

OTHER PUBLICATIONS

Devices for Vascular Intervention, Inc. Brochure, "DVI Guiding Catheters for Directional Atherectomy in the RCA", copyright 1993.

*Primary Examiner*—Max Hindenburg
*Assistant Examiner*—Pamela L. Wingood
*Attorney, Agent, or Firm*—Nawrocki, Rooney & Silvertson, P.A.

[57] ABSTRACT

Guide catheter incorporating a braidless construction having increased performance characteristics for catheterization procedures. The guide catheter may include a tracking wire, inner or outer guide for positioning the guide catheter within the patient's vascular system.

21 Claims, 6 Drawing Sheets

BRAIDLESS GUIDE CATHETER

BACKGROUND OF THE INVENTION

1. Field of the Invention

The present invention relates to guide catheters and diagnostic catheters used in medical catheterization procedures. In particular, the present invention relates to an improved guide or diagnostic catheter having a simple, braid-free catheter design, which is capable of performing the functions of conventional diagnostic and guide catheters.

2. Description of the Prior Art

Guide catheters and diagnostic catheters are well known for use in coronary catheterization and percutaneous transluminal coronary angioplasty (PTCA) procedures. Guide catheters aid in treatment of arterial lesions by providing a conduit for positioning dilatation balloon systems across an arterial stenosis. Guide catheters and diagnostic catheters work with various assemblies for performing other medical, therapeutic, and diagnostic procedures, such as dye delivery, arterial flushing, or arterial pressure monitoring.

Diagnostic catheters are used during cardiac catheterization for diagnosis of coronary artery disease in order to define vessel anatomy, isolate lesions, and identify adjacent cardiac branches which may impinge on the lesion and affect ventricular function.

For diagnosis of the coronary artery, the femoral artery is entered percutaneously and a sheath is inserted into the artery to provide access to the patient's vascular system. The diagnostic catheter is inserted into the femoral artery through this introducer sheath over a guide wire and advanced up the aorta to the aortic arch. Once over the aortic arch, the guide wire may be removed. A Y-adapter and manifold assembly are attached to the diagnostic catheter for implementation of diagnostic procedures, such as dye delivery, flushing capabilities, and arterial pressure monitoring.

The diagnostic catheter design generally includes a shaft having a proximal and a distal end. A lumen extends longitudinally through the shaft from the proximal to the distal end. Operably connected to the proximal end of the shaft is a hub assembly, for connection to catheterization equipment, and connected to the distal end of the shaft is a soft tip.

The distal end of the guide catheter shaft is shaped to access the ostium of the coronary artery having the stenotic lesion. Different shapes may be employed for access to the ostium of a right or left coronary artery, mammary artery or the ostium of a bi-pass vein. During the diagnosis procedure, the physician advances and maneuvers the diagnostic catheter shaft within the artery, while at the same time injecting dye. The physician observes the dye using an angiography monitor for visualization of the patient's coronary system.

The diagnostic catheter is advanced and maneuvered until the distal end is properly engaged in the ostium of the coronary artery the physician believes to contain the stenosis. Once seated in the ostium, the physician injects additional dye for observations of obstruction to dye flow, indicative of the coronary disease.

For treatment of the coronary disease through angioplasty or other catheter based treatments, guide catheters are used. The guide catheters provide access to the area within the arterial system containing the stenotic lesion, and support for the treatment catheter which often includes a balloon dilatation system. Guide catheters similar in construction to diagnostic catheters, although they are generally larger in size. Prior art guide catheters typically have a pre-shaped distal section or tip region to aid in access to the ostium of the coronary artery to receive treatment.

In operation, the guide catheter is introduced over a guide wire through a previously placed femoral introducer sheath and advanced up to the aortic arch. The guide wire can then be removed, and the guide catheter can be advanced and maneuvered until the guide catheter soft tip is properly engaged in the ostium of the coronary artery to be dilatated. A Y-adapter and manifold assembly are attached to the guide catheter hub at the proximal end for implementation of therapeutic procedures, such as dye delivery, flushing capabilities, pressure monitoring and delivery of the dilatation balloon system.

Diagnostic catheters and guide catheters are manufactured in hundreds of shapes and curve styles to accommodate anatomical variances in humans and to access specific areas within the coronary system. Curve shapes are also designed to provide support against the aortic wall when seated within the ostium, to resist the tendency for a catheter to "pop out" of the ostium (termed backout force) when injecting dye or advancing a treatment catheter into the artery. Catheters are presently specifically manufactured with high curve retention to maintain catheter placement within the ostium and to resist backout forces.

During angioplasty procedures, the catheters must be able to traverse tortuous pathways through blood vessels to the stenosis in a manner as atraumatic as possible. Therefore, to limit insertion time and discomfort to the patient, the catheter must be stiff enough to resist the formation of kinks, while at the same time the catheter must possess flexibility to be responsive to maneuvering forces when guiding the catheter through the vascular system. It is important that the guide catheter exhibit good torque control such that manipulation of a proximal portion of the guide catheter is responsively translated to the tip or distal end of the catheter to curve and guide the catheter through the tortuous pathways.

To meet the above performance requirements, guide catheters and diagnostic catheters are manufactured using polymers in conjunction with a braid of high-strength fibers or stainless steel wires incorporated into the tube. The guide catheters are generally formed of three layers: a first inner layer commonly formed of polytetrafluoroethylene to decrease the coefficient of friction between a balloon catheter and the guide catheter; a middle layer consisting of braided wire for torque control; and a third, outer layer commonly formed of polyethylene, polyurethane, polyether blocked amide (PEBA) or a nylon-blend for stable positioning of the guide catheter, and providing backout support during other treatment procedures.

During diagnostic and therapeutic procedures, it is often necessary to use more than one shaped or curved catheter to access the right coronary, left coronary, mammary artery, or bipass vein for visualization of each vessel. The procedure of exchanging diagnostic catheters for visualization of different vessels requires more procedural time and exposes the patient to extended x-ray time and fluoroscopy. Additionally, hospitals are required to inventory hundreds of catheters with various curves, tip shapes and diameters to accommodate the various procedures for each patient.

It is desirable in catheter design for the inside diameter of the diagnostic or guide catheter to be maximized relative to the outside diameter, providing maximum space for dye flow and dilatation catheter delivery. While designing catheters to meet these design goals, the catheters must continue to meet performance requirements of burst pressure requirements, kink resistance, curve retention, column strength, and torque control for advancement within the patient's vascular system.

SUMMARY OF THE INVENTION

The present invention relates to an improved guide or diagnostic catheter having a simple braid-free catheter design, capable of performing the function of conventional diagnostic and guide catheters.

In a preferred embodiment, the catheter of the present invention is for use as a guide or diagnostic catheter in catheter procedures. The catheter includes a generally elongate shaft formed of a single polymeric layer having a proximal end and a distal end. A lumen extends longitudinally between the proximal end and the distal end. Means are included within the lumen of sufficient diameter for supporting the shaft during the catheter placement. The means for supporting the shaft may include a core wire having a nonmetallic coating. The means for supporting the shaft may be curved, or alternatively, the shaft may be curved.

The means for supporting the shaft may alternately include a second shaft for insertion into the lumen during the catheter procedure. The second shaft may include an elongate tubular member also having a lumen extending longitudinally therethrough. The catheter assembly may include means for securing the proximal end of the shaft to the proximal end of the second shaft. In an alternative embodiment, the means for supporting the shaft is positioned over the shaft.

The present invention further includes a method of supporting a guide or diagnostic catheter for positioning the catheter within a patient's vascular system. An elongate shaft formed of a single layer of polymeric material is provided which is inserted within the patient's vascular system. An elongate tubular member formed of a polymeric material is advanced over the shaft, the shaft being of sufficient diameter for transmitting forces between the tubular member and the shaft. A distal end of the tubular member is positioned within the patient's vascular system. The shaft may include a core having a polymeric coating. The distal end of the shaft may be positioned within the ostium of the coronary to receive treatment.

Alternatively, the shaft may include a second tubular member formed of a polymeric material. The proximal end of the second tubular member may be locked to the proximal end of the shaft. The distal end of the second tubular member may be engaged in the ostium of a coronary within the vascular system.

Alternatively, the distal end of the first tubular member may extend beyond the distal end of the second tubular member, and the distal end of the first tubular member is engaged within the ostium of a coronary within the vascular system. The second tubular member is advanced, tracking over the first tubular member until the distal end of the second tubular member is engaged in the ostium. The first tubular member is removed from the patient's vascular system. Alternatively, the second tubular member may be removed from the patient's vascular system.

The present invention provides an economically feasible diagnostic or guide catheter design which may be universally usable for most anatomical situations. The catheter of the present invention is less costly to manufacture than conventional catheters, while meeting performance requirements for use, including kink-resistance, curve retention, column strength and torque control.

BRIEF DESCRIPTION OF THE DRAWINGS

The invention will be further described with reference to the accompanying drawings where like numbers refer to like parts in several views and wherein.

DETAILED DESCRIPTION OF THE PREFERRED EMBODIMENTS

The present invention relates to an improved guide or diagnostic catheter having a simple, braid-free design, which is capable of performing the functions of conventional diagnostic and guide catheters, while increasing lumen size back up support, radiopacity during placement, and dye control. The present invention provides an economically feasible diagnostic or guide catheter design which may be universally useable for most anatomical situations. The catheter of the present invention is less costly to manufacture than conventional catheters, while meeting performance requirements for use, including kink resistance, curve retention, column strength and torque control. Although references throughout this specification may be specifically made to either guide catheters or diagnostic catheters, references made to one or the other are equally applicable to guide catheters and diagnostic catheters, coronary, neuro, general peripheral, and any vascular type catheters.

The focus of technology for guide and diagnostic catheters has centered around designs which provide kink resistance and torque response within a catheter tubular member. Kink resistance and torque response are necessary so that manipulation of a proximal portion of the catheter is responsively translated to the tip or distal end of the catheter to curve and guide the catheter through the tortuous pathways of a patient's vascular system, to direct and position the distal tip of the catheter near the coronary area receiving treatment while maintaining an open lumen for the treatment procedure.

To achieve these performance characteristics, guide catheter designs have generally included a tubular member formed of three layers, which include braiding or coiling integral to the catheter tube construction. The inner layer can be formed of a polytetrafluoroethylene or lubricous polymer to decrease the coefficient of friction between the balloon catheter or other device and the guide catheter. The middle layer consists of braided or helically wrapped wires or filaments, for torque control. The outer layer is generally a polymeric layer which gives the catheter stable positioning within the patient's vascular system by providing backup support during catheter procedures. The outer layer is typically formed of a polyethylene, polyurethane, polyether blocked amide or nylon-blend. Additionally, the outer layer usually is impregnated with a radiopaque material, such as barium sulfate or bismuth subcarbonate, to allow for partial visualization of the catheter shaft during the catheter procedure.

Braided catheter designs are manufacturing intensive, requiring additional costs, time, and manufacturing space. Additionally, braided catheter designs have performance limitations, including a larger wall thickness to accommodate the braided middle layer which limits available lumen diameter for a given outside diameter.

The primary function of the braided middle layer, is to provide sufficient torque and kink performance to the catheter body for properly positioning the guide catheter within the coronary anatomy. Once the catheter is positioned within the patient's vascular system, the need for catheter kink and torque performance is no longer necessary.

The present invention provides a catheter (guide or diagnostic) which can be effectively positioned within the patient's coronary anatomy, without utilizing a braided middle layer. The guide catheter of the present invention includes the use of a tracking wire which may be positioned into the selected coronary artery and allows the guide catheter to be tracked over the tracking wire into the same coronary artery.

Figure 1:
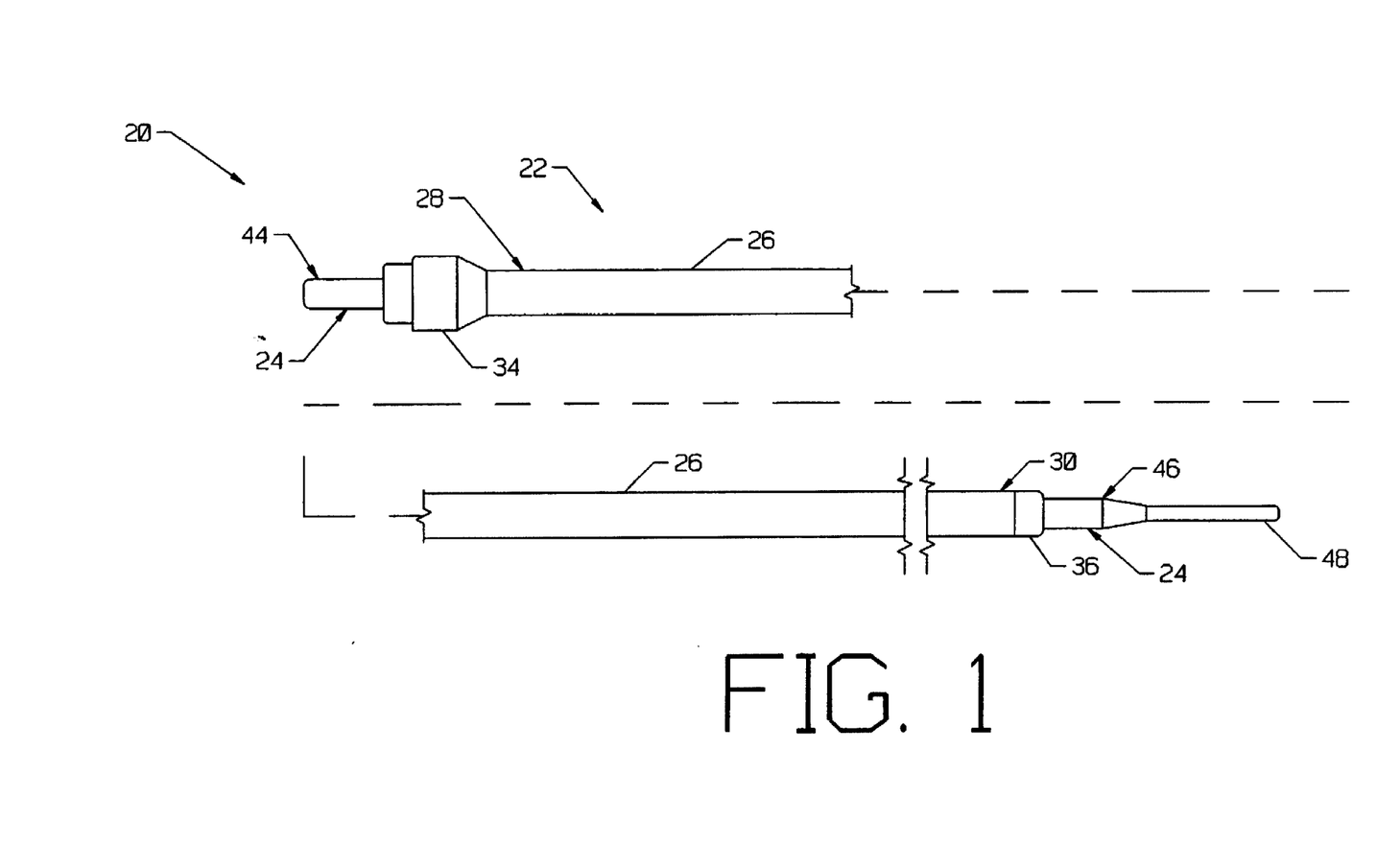
FIG. 1 is a perspective view of a catheter of the present invention having a tracking wire disposed therein.

FIG. 1 shows a perspective view of the braidless guide catheter assembly 20 in accordance with the present invention. The catheter assembly 20 includes a guide catheter 22 positioned over a tracking wire 24. The tracking wire 24 provides the guide catheter 22 with the required performance torque response and kink resistance necessary for guiding the guide catheter 22 through the tortuous pathways of a patient's vascular system.

The guide catheter 22 includes a shaft 26 having a proximal end 28 and a distal end 30. A lumen 32, shown in FIG. 1A, extends longitudinally through the shaft from the proximal end 28 to the distal end 30. Operably connected to the proximal end 28 of the shaft 26 is a hub assembly 34, and connected to the distal end 30 of the shaft 26 is a soft tip 36.

Figure 1A:
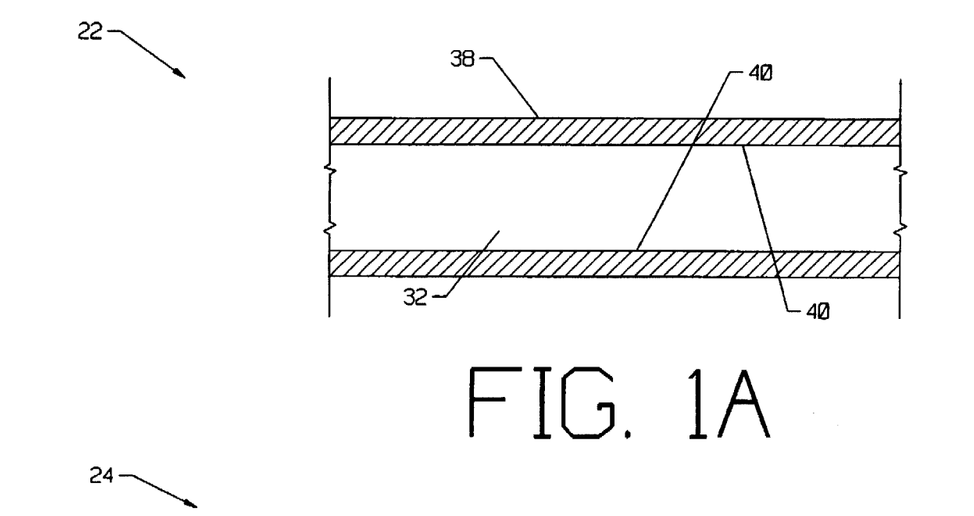
FIG. 1A is a partial sectional view of the catheter of FIG. 1.

The guide catheter 22 shaft 26 is formed of a single extruded polymer layer 38 with or without a lubricous inner coating 40. It is recognized that shaft 26 may be formed by a co-extrusion process. In a preferred embodiment, layer 38 is formed of polyether blocked amide, polyethylene, polyurethane or a nylon blend. The layer 38 provides for stable positioning within a patient's vascular system and backup support during catheter procedures. Preferably, the layer 38 is impregnated with a radiopaque material, such as barium sulfate or bismuth subcarbonate, to allow for partial visualization of the shaft 26 during catheter procedures.

The lubricous inner coating 40 allows for near frictionless movement of the tracking wire 24 within the guide catheter lumen 32. In a preferred embodiment, the lubricous inner coating is a hydrophilic coating. Alternatively, the guide catheter 22 may include an inner layer formed of a lubricous polymer, such as polytetrafluoroethylene.

The absence of a braided layer within the guide catheter 22 allows the guide catheter 22 to have a larger inside diameter relative to conventional guide catheters of a given outside diameter which include the braided middle layer. By maximizing the inside diameter relative to the outside diameter, the guide catheter 22 is able to provide increased performance, including maximum dye flow and maximum catheter delivery size.

The absence of the braided layer provides two alternative guide catheter constructions. Preferably, the absence of the middle layer allows the catheter design to have an internal diameter larger than is available in conventional guide catheters, while continuing to provide the same amount of curve retention and backup support to the guide catheter. In one embodiment, the internal diameter of the guide catheter 22 is approximately 5 to 10 percent larger than the conventional braided guide catheter having the same outside diameter with equivalent back-up and curve retention performance. In the second alternative, additional polymer may be added to the shaft 26 layer 38 to increase the catheter wall volume. The additional polymer provides additional backup support to the guide catheter 22 during catheter treatment procedures.

Figure 1B:
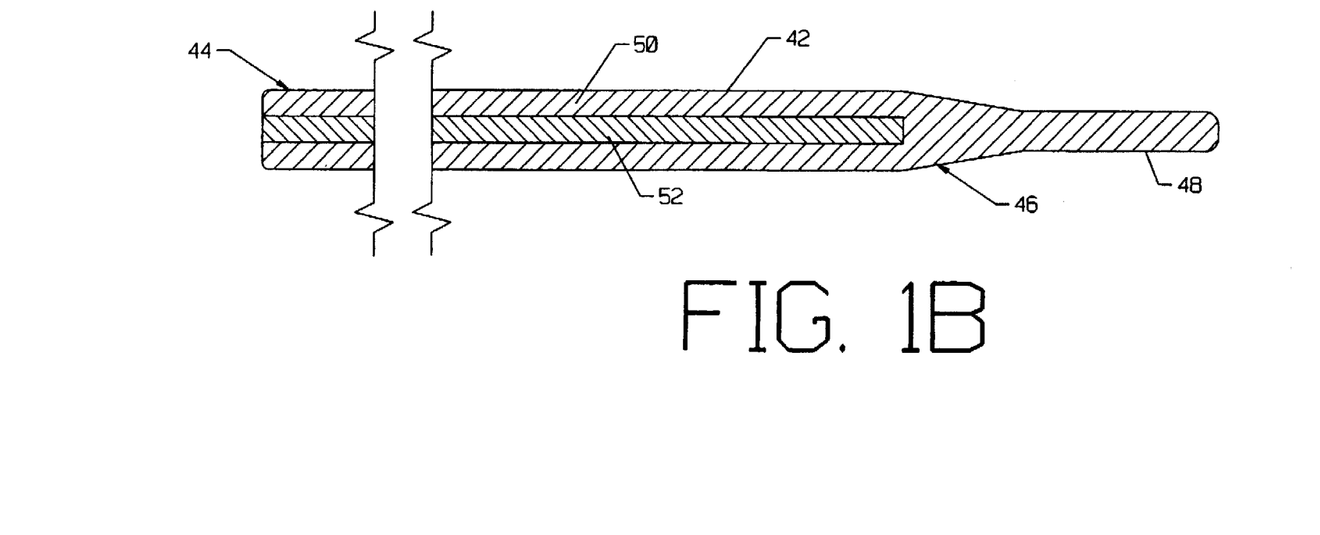
FIG. 1B is a sectional view of the catheter tracking wire of FIG. 1.

Referring to FIG. 1B, a cross-sectional view of the tracking wire 24 of FIG. 1 is generally shown. The tracking wire 24 includes an elongate shaft 42 having a proximal end 44 and a distal end 46. Located at the distal end 46 is a soft tip 48.

The shaft 42 includes an outer layer 50 formed over a core 52. The core 52 extends from the proximal end 44 to the distal end 46, but does not extend through the soft tip 48. In a preferred embodiment, the core is wire, formed from stainless steel, a nickel titanium alloy (or Nitinol), or other material which provides sufficient strength and support. The outer layer 50 is formed of polymer, preferably polyether blocked amide, polyethylene, polyurethane or nylon blend. The outer layer 50 can be impregnated with a radiopaque material, such as barium sulfate or bismuth subcarbonate, for visualization of the shaft during catheter procedures.

In a preferred embodiment, the specialty wire 24 is formed by positioning a polymer sleeve over a stainless steel wire. The wire and polymer sleeve are pulled through a heated die, forming the polymer sleeve over the stainless steel wire. The outer layer 50 is then coated with a lubricous substance to aid in movement of the specialty wire 24 through the guide catheter 22 lumen 32. In a preferred embodiment, the lubricous outer coating is a hydrophilic coating. Alternatively, the specialty wire 24 may be formed by other extrusion or co-extrusion processes as known in the art.

The tracking wire 24 soft tip 48 is formed of soft polymer extending beyond the core 52. The tip 48 may be of a uniform outside diameter or preferably, the tip 48 is tapered for safer ostial engagement.

The guide catheter 22 is preferably straight, however the guide catheter 12 may be curved and shaped for access to specific coronary regions. With a straight guide catheter, the tracking wire 24 may be curved and shaped. With a curved tracking wire 24, the tracking wire 24 is advanced within a patient's vascular system until the soft tip 48 is engaged in the ostium of the coronary artery to be treated. The guide catheter 22 is then advanced over the specialty wire 24 until the guide catheter soft tip 36 is similarly engaged in the ostium of the coronary artery receiving treatment.

During an angioplasty procedure, the femoral artery is entered percutaneously and a sheath is inserted into the artery to provide access to the patient's vascular system. The tracking wire 24 is inserted into the femoral artery through the introducer sheath and advanced up to and over the aortic arch. The tracking wire 24 is advanced and torqued until the tip 36 is engaged in the ostium of the coronary artery receiving treatment. Next, the guide catheter 22 is inserted into the femoral artery through the introducer sheath, over the tracking wire 24.

The guide catheter 22 tracks the tracking wire 24 during advancement through the patient's vascular system. The guide catheter 22 is advanced over the tracking wire 24 until the distal end 30 passes over the aortic arch. As the guide catheter 22 is advanced over the tracking wire 24, through a patient's vascular system, the tracking wire 24 provides the kink and torque performance of conventional braided guide catheter designs.

With the soft tip 36 of the tracking wire 24 engaged in the ostium of the coronary receiving treatment, the guide catheter is advanced over the tracking wire until the guide catheter soft tip 36 is similarly engaged in the ostium of the coronary receiving treatment. Once the guide catheter 22 is positioned within the ostium of the coronary artery receiving treatment, the need for kink and torque performance is no longer necessary and the tracking wire 24 may be removed.

Once the tracking wire 24 is removed, the guide catheter 22, including a larger lumen 32, is able to provide the physician with increased dye delivery, and a larger lumen for accommodating a larger balloon dilatation catheter.

In a preferred embodiment, the tracking wire 24 has an outside diameter of 0.038" for use with 5F, 6F and 7F catheters and 0.063" for use with 8F, 9F and 10F catheters. It is also recognized that the tracking wire 24 may be used by the physician for guide catheter exchange procedures for exchanging to a larger guide catheter. The tracking wire 24 would provide stability and support during removal and exchange of the guide catheter. Preferably, the tracking wire 24 would include a magnetically responsive/active section at its proximal end, which can be similar to the magnetic sections disclosed in the catheter exchange devices in application Ser. Nos. 08/048,492 and 07/929,083. The tracking wire 24 would then be used for guide catheter exchange procedures, which can be similar to those disclosed in application Ser. No. 08/397,578 for use with magnetic exchange devices. Application Ser. Nos. 07/929,083; 08/048,492; and 08/397,578 is herein incorporated by reference.

Figure 2:
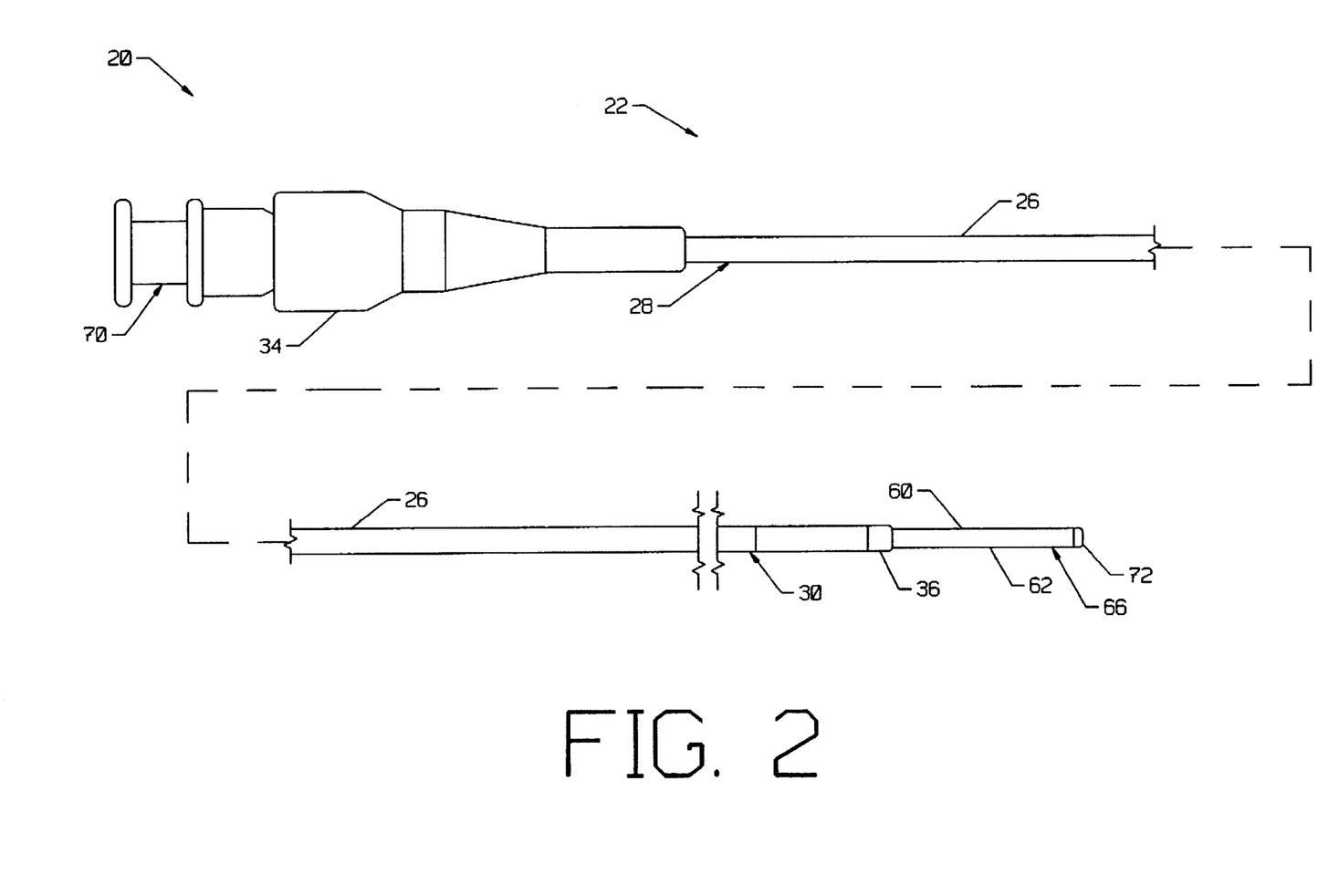
FIG. 2 is a perspective view showing an alternative embodiment of the catheter of the present invention having an inner guide disposed therein.

Referring to FIG. 2, another embodiment of the guide catheter assembly 20 of the present invention is generally shown. The catheter assembly 20 includes a guide catheter 22 and an inner guide member 60. The construction of the guide catheter 22 can be similar to the construction of the guide catheter 22 shown and described previously in FIG. 1. The catheter assembly 20 with the inner guide 60 provides the physician with a guide catheter that has a simple, braid-free catheter design, which is capable of performing the functions of conventional guide catheters.

Figure 2A:
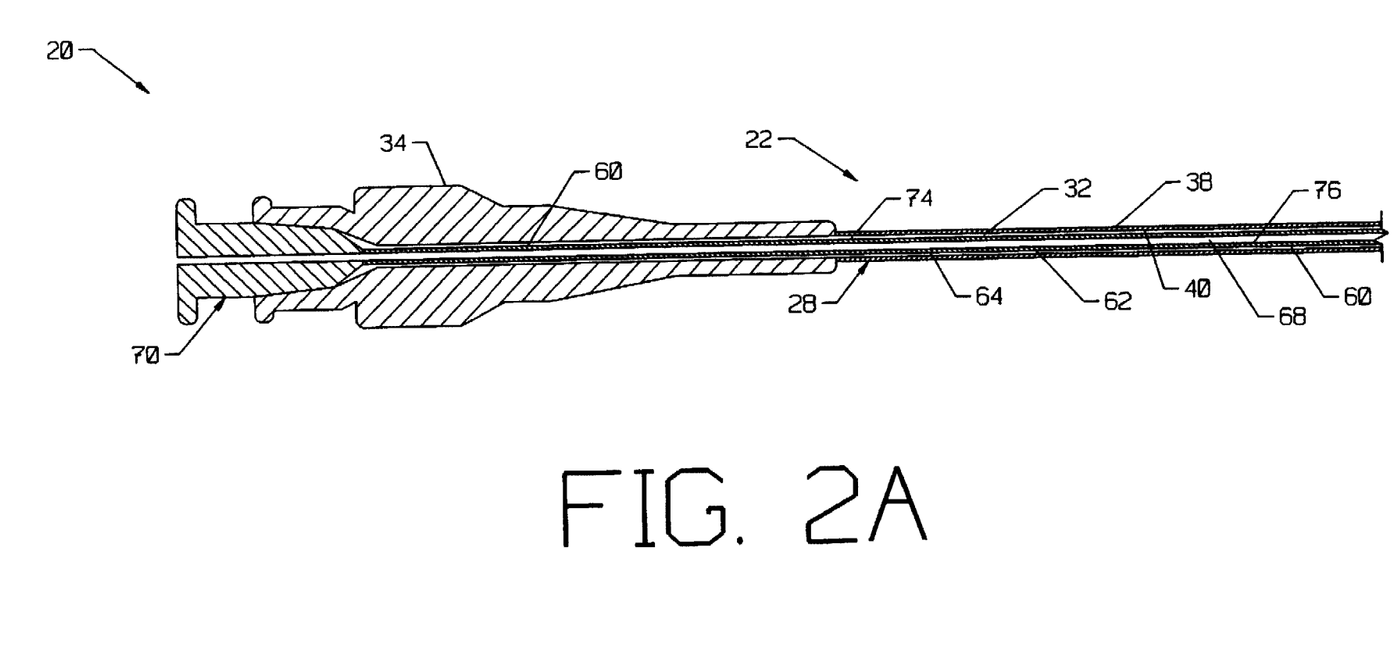
FIG. 2A is a partial sectional view showing the catheter of FIG. 2.
Figure 2B:
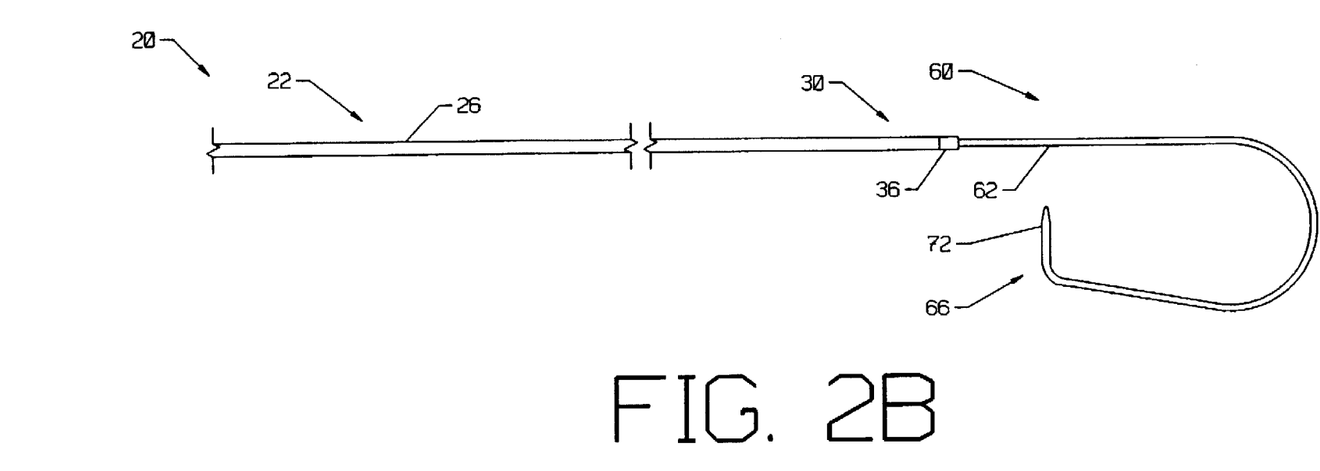
FIG. 2B is a partial perspective view showing an alternative embodiment of the catheter of FIG. 2.

Referring to FIGS. 2, 2A and 2B, the inner guide 60 generally includes a shaft 62 having a proximal end 64 and a distal end 66. A lumen 68 extends longitudinally through the shaft 62 from the proximal end 64 to the distal end 66. Operably connected to the proximal end 64 of the shaft 62 is a hub assembly 70, for connection to catheterization equipment, including the hub assembly 34 of guide catheter 22. Connected to the distal end 66 of the shaft 62 is a soft tip 72, which may be tapered.

The inner guide 60 is formed using extrusion processes which can be similar to the formation of the guide catheter 22. In a preferred embodiment, the inner guide 60 includes a single layer 74 formed of extruded polymer, preferably fiber filled with liquid crystal polymer (LCP), glass fiber, Kevlar fiber, carbon fiber, or other similar fiber. Alternatively, the inner guide 60 may be multilayered.

The single layer 74 is formed of a polymeric material, such as polyether blocked amide, polyethylene, polyurethane, or a nylon blend, for stable positioning, kink-resistance, and torque control of the guide catheter 22.

Due to the relatively thin walls of guide catheter 22 and inner guide 60, the inner guide 60 may also be impregnated with radiopaque materials such as barium sulfate, or bismuth subcarbonate for visualization of the shaft during catheterization procedures. In the preferred embodiment, the inner guide 60 single layer 74 is formed of a polyether blocked amide or PEBA impregnated with 20–60 percent radiopaque materials having a relatively high durometer.

The outside diameter of the inner guide 60 is sized for slidable insertion within the lumen of the guide catheter 22. The outside diameter of the inner guide 60 is of sufficient size to provide support, torqueability, and kink-resistance to guide catheter 22 for positioning guide catheter 27 within the patient's coronary anatomy. The inside diameter of the inner guide 60 lumen 68 is sized to accommodate standard catheter procedure guide wires. In the preferred embodiment, the inside diameter of inner guide 60 lumen 68 is between 0.038 and 0.040 inches to accommodate 0.035 inch guide wires.

When the inner guide 60 is inserted within the guide catheter 22 lumen 32, the inner guide hub assembly 70 connects to the guide catheter 22 hub assembly 34. By locking the inner guide 60 hub assembly 70 to the guide catheter 22 hub assembly 34, the inner guide 60 may be used to position and torque the guide catheter 22 into the desired location in the coronary anatomy. The inner guide 60 provides support, kink-resistance, and torquability to the braidless guide catheter 22 during introduction and positioning of the guide catheter within the patient's vascular system. The inner guide 60 may or may not extend beyond the distal end 30 of guide catheter 22.

With the inner guide 60 hub assembly 70 locked to the guide catheter 22 hub assembly 34, dye may be injected into the patient's vascular system through the inner guide 60 lumen 68. By injecting dye through the inner guide lumen 68, the amount of dye released into the patient's system may be easily controlled, especially where the inner guide 60 is positioned within a larger size catheter. In the preferred embodiment, the outside diameter of the inner guide 60 varies relative to the size of guide catheter 22, but the inside diameter of inner guide is constant, preferably approximately 0.038 inches. A Y-adaptor and manifold assembly may be attached to the catheter assembly 20 including the guide catheter 22 and inner guide 60 for contrast dye and flush delivery and pressure monitoring. Additionally, by locking the inner guide hub assembly 70 with the catheter hub assembly 34, the catheter assembly 20 acts as an anti-bleeding device for preventing back bleeding through the guide catheter 22.

In use, the femoral artery is entered percutaneously and a sheath is inserted into the artery to provide access for the catheter assembly 20 to the patient's vascular system. The guide wire, preferably a 0.035 inch wire, is inserted through the femoral sheath into the patient's vascular system and advanced up and over the aortic arch. The inner guide 60 is inserted into the guide catheter 22, with hub assembly 70 locked to hub assembly 34, to form catheter assembly 20. The catheter assembly 20 is introduced over the guide wire through the femoral introducer sheath and advanced up to the aortic arch. As the catheter assembly 20 is advanced up and over the aortic arch, the inner guide 60 provides support, kink-resistance, and torquability to the braidless guide catheter 22.

After advancing the catheter assembly 20 over the aortic arch, the guide wire can then be removed. A Y-adaptor and manifold assembly are attached to the catheter assembly 20 for injection of dye contrast, flush delivery, and pressure monitoring. The contrast media allows the physician to locate the ostium for seating the guide catheter 22.

The catheter assembly 20 is now advanced and torqued until it is engaged in the ostium of the vessel which is to receive treatment. Once the guide catheter 22 is engaged within the desired ostium, the inner guide 60 may be removed. The luer attached to the inner guide hub assembly 70 and the catheter hub assembly 34 is unlocked, and the inner guide hub assembly 70 is disconnected from the catheter hub assembly 34. The inner guide 60 is pulled out and removed.

The inner guide 60 provides torquability and kink-resistance to the guide catheter 22 for positioning the guide catheter 22 within the patient's coronary anatomy. Once the guide catheter 22 is correctly positioned within the patient's coronary system, the need for kink-resistance and torquability is no longer necessary, and the inner guide 60 may be removed. After removal of the inner guide 60, the physician may proceed with treatment of the diseased area, such as through the use of a balloon dilatation system, as the physician would when using a conventional guide catheter.

In a preferred embodiment, the inner guide 60 may be curved or shaped, and guide catheter 22 straight. The curved inner guide 60 would give shape to the catheter assembly 20 for accessing specific areas within the patient's coronary anatomy. Alternatively, it is recognized that the same function may be accomplished by providing a straight inner guide 60 with a curved or shaped guide catheter 22.

In one preferred embodiment for smaller catheter sizes, such as 5F, 6F, or 7F, the inner guide 60 is curved or shaped, and the guide catheter 22 is curveless or straight. Referring to FIG. 2B, the inner guide 60 distal end 66 extends beyond the guide catheter 22 distal end 30. With the catheter assembly 20 advanced over the aortic arch, the inner guide 60 distal end 66 (and specifically tip 72) is engaged in the ostium of the vessel to receive treatment. The guide catheter 22 is tracked over the inner guide 60 until the distal end 30 is similarly engaged in the ostium to receive treatment.

The inner guide, which is curved or shaped, is then removed. The curveless guide catheter 22 is positioned within the ostium of the coronary artery receiving treatment. The curveless guide catheter 22 provides better support to the treatment system while being less traumatic to the patient's vascular system than a shaped catheter system, which would induce preformed stresses within the vessels due to its curved structure.

Figure 2C:
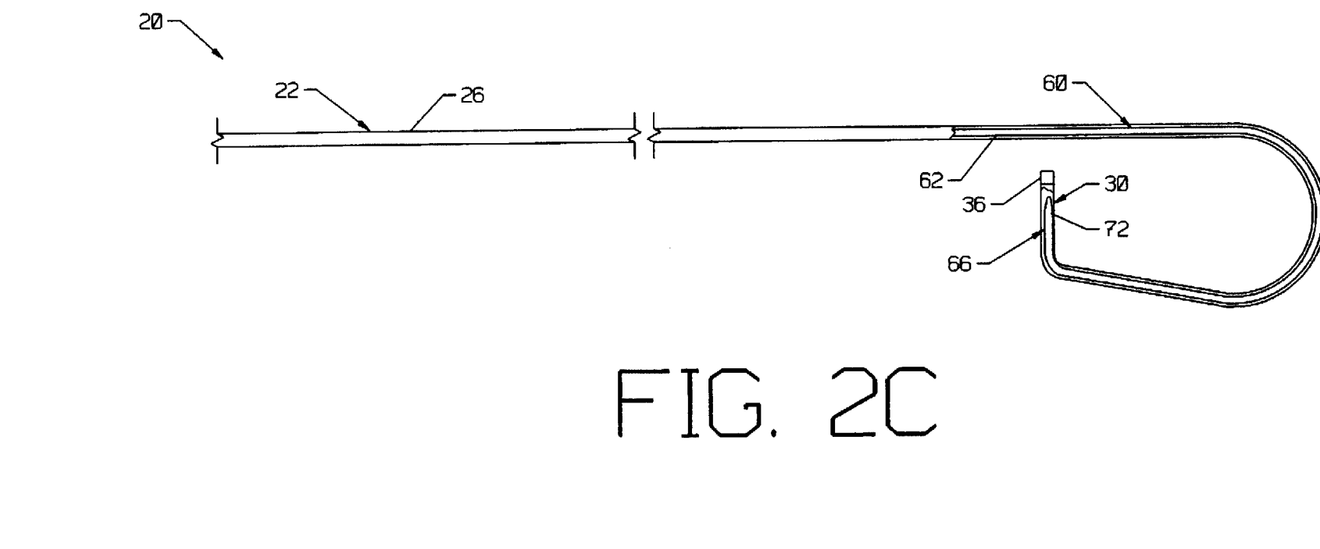
FIG. 2C is a partial perspective view with a partial cutaway showing an alternative embodiment of the catheter of FIG. 2.

In another preferred embodiment for larger catheter sizes, such as 8F, 9F and 10F, the inner guide 60 is curveless and the guide catheter 22 is curved or shaped. Referring to FIG. 2C, the guide catheter 22 distal end 30 extends beyond the inner guide 60 distal end 66. The inner guide 60 provides torqueability and kink resistance to guide catheter 22 for positioning the guide catheter 22 within the patient's coronary anatomy. Once the catheter assembly 20 is advanced over the aortic arch, the catheter assembly 20 is torqued and advanced until the guide catheter 22 distal end 30 is engaged in the ostium of the vessel to receive treatment.

Once the guide catheter 22 is correctly positioned within the patient's coronary system, the need for kink resistance and torqueability is no longer necessary, and the inner guide 60 may be removed. After removal of the inner guide 60, the physician may proceed with treatment of the diseased area, such as through the use of a balloon dilatation system, as the physician would when using a conventional guide catheter.

Figure 2D:
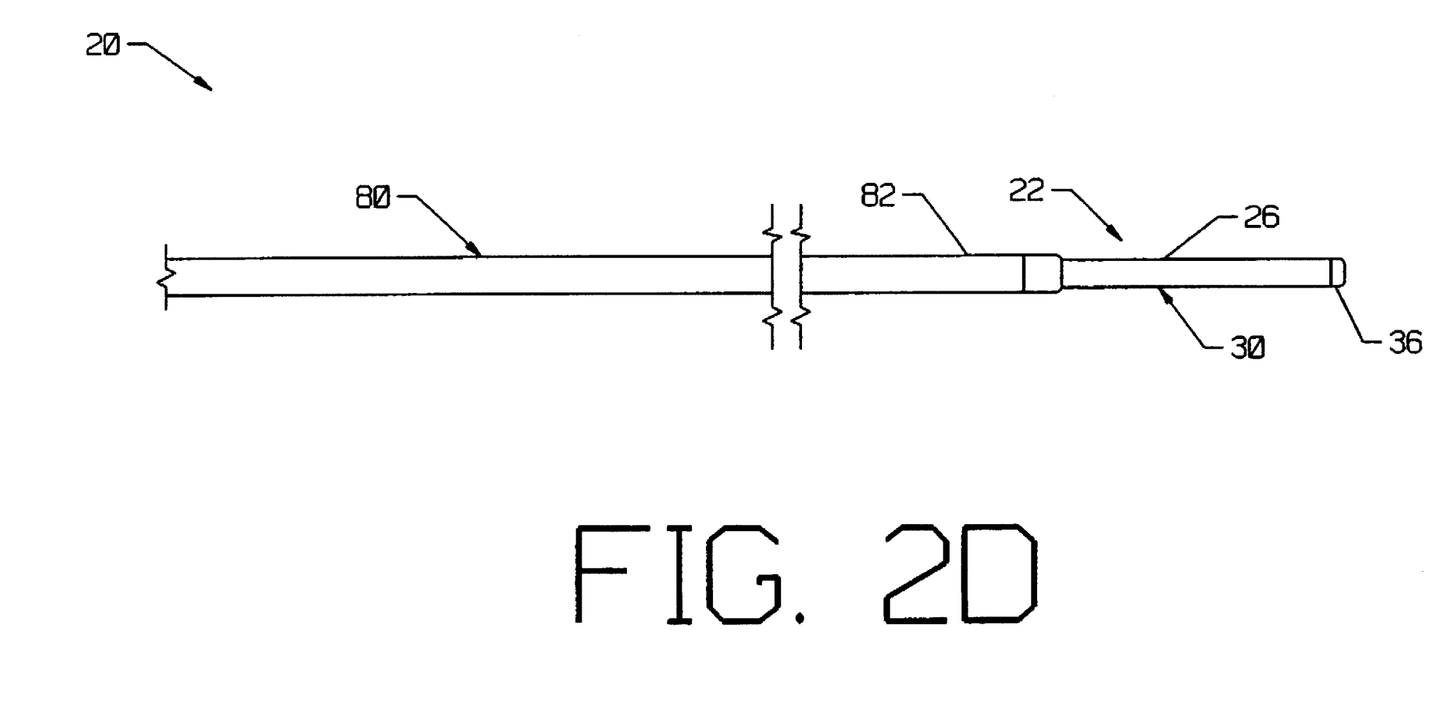
FIG. 2D is a perspective view showing another alternative embodiment of the catheter of the present invention having an outer guide.

Referring to FIG. 2D, yet another embodiment of the present invention is shown. The catheter assembly 20 includes a guide catheter 22 and an outer guide 80. The outer guide 80 can be similar in construction to the inner guide 60 which was previously detailed herein. Similarly, the outer guide 80 provides the same function as previously described inner guide 60, in that it provides torqueability and kink resistance to the guide catheter 22 for positioning the guide catheter 22 within the patient's coronary anatomy. Once the guide catheter 22 is correctly positioned within the patient's coronary system, the need for kink resistance and torqueability is no longer necessary, and the outer guide 80 may be removed. After removal of the outer guide 80, the physician may proceed with treatment of the diseased area, such as through the use of a balloon dilatation system, as the physician would when using a conventional guide catheter.

The outer guide 80 may be curved or shaped, and the guide catheter 22 curveless or straight. The curved outer guide 80 would give shape to the catheter assembly 20 for accessing specific areas within the patient's coronary anatomy. Alternatively, it is recognized that similar functions may be accomplished by providing a straight or curveless outer guide 80 with a curved or shaped guide catheter 22. The guide catheter 22 may or may not extend beyond a distal end 82 of the outer guide 80. In use, the outer guide 80 functions similar to inner guide 60 during catheterization procedures. The femoral artery is entered percutaneously, and a sheath is inserted into the artery to provide access for the catheter assembly 20 to the patient's vascular system. A guide wire is inserted through the femoral sheath into the patient's vascular system and advanced up over the aortic arch. The outer guide 80 is positioned over the guide catheter 22 to form catheter assembly 20. The outer guide 80 and guide catheter 22 may be secured together at their proximal ends using a hub assembly similar to that previously described herein, or they may be secured together by other means, such as the use of magnetically active segments which can be similar to those disclosed in U.S. application Ser. Nos. 07/929,083; 08/048,429; and 08/369,190 for use with magnetic devices. U.S. application Ser. Nos. 07/929,083; 08/048,429; and 08/369,190 has been previously incorporated into this application by reference.

The catheter assembly 20 is introduced over the guide wire through the femoral introducer sheath and advanced up to and over the aortic arch. As the catheter assembly 20 is advanced up and over the aortic arch, the outer guide 80 provides support, kink resistance, and torqueability to the braidless guide catheter 22.

After advancing the catheter assembly 20 over the aortic arch, the guide wire can be removed. A Y-adapter and manifold assembly may be attached to the catheter assembly 20 for injection of die contrast, flush delivery, and pressure monitoring. The contrast media allows the physician to locate the ostium for seating the guide catheter 22.

The catheter assembly 20 is now advanced and torqued until it is engaged in the ostium of the vessel which is to receive treatment. The guide catheter 22 distal end 36 may be engaged in the ostium. Alternatively, if the outer guide 80 extends beyond the guide catheter 22, the outer guide 80 distal end 82 may be engaged within the coronary ostium, and then the guide catheter 22 distal end 30 may be advanced and similarly engaged in the ostium of the coronary to receive treatment. Once the guide catheter 22 is correctly positioned within the patient's coronary system, the need for kink resistance and torqueability is no longer necessary, and the outer guide 80 may be removed. After removal of the outer guide 80, the physician may proceed with treatment of the diseased area, such as through the use of a balloon dilatation system, as the physician when using a conventional guide catheter.

The guide catheter assembly 20 of the present invention, would provide for increased performance during diagnostic procedures. The dimensions of the diagnostic catheter could be scaled appropriately and constructed to withstand adequate burst pressures for high pressure dye delivery typical of diagnostic procedures. The present invention would allow the physician to use diagnostic catheter shapes for visualizing various areas of the coronary system, without having to remove the diagnostic catheter from the patient's body. The time saving procedure using the present invention also results in less patient exposure to fluoroscopy.

The present invention provides a catheter which can be effectively positioned within the patient's coronary anatomy, without utilizing a braided middle layer. The absence of a braided layer within the guide catheter allows the guide catheter to have a lumen with a larger inside diameter relative to conventional guide catheters of a given outside diameter formed of braided construction. By maximizing the inside diameter relative to the outside, the guide catheter is able to provide increased performance, including maximum dye flow and maximum catheter delivery size. Additionally, the guide catheter of the present invention provides equivalent back-up and curve retention performance to that of conventional guide catheters.

It will be understood, that this disclosure is, in many respects, only illustrative. Changes may be made in details, particularly in matters of shape, size, material, and arrangement of parts without exceeding the scope of the invention. Accordingly, the scope of the invention is as defined within the language of the appended claims.

What is claimed is:

1. A braidless catheter assembly for use as a guide catheter in catheter procedures comprising:
    a generally elongate shaft formed of a polymeric layer having a proximal end and a distal end, with a lumen extending longitudinally between the proximal end and the distal end; and
    means insertable within the lumen of sufficient outside diameter for continual slidable contact with the shaft, thereby supporting and guiding the shaft during catheter placement.

2. The catheter assembly of claim 1, wherein the means insertable within the lumen includes:
    a support member having a core wire and a nonmetallic coating thereon.

3. The catheter assembly of claim 2, wherein the support member is generally elongate having a proximal end and a distal end with a soft tip located at the distal end.

4. The catheter assembly of claim 3, wherein the support member distal end is tapered.

5. The catheter assembly of claim 1, wherein the means insertable within the lumen is curved.

6. The catheter assembly of claim 1, wherein the shaft is curved.

7. The catheter assembly of claim 1, wherein the means insertable within the lumen comprises:
    a second shaft having an outside diameter less than the diameter of the lumen for insertion into the lumen during the catheter placement.

8. The catheter assembly of claim 7, wherein the second shaft is an elongate tubular member.

9. The catheter assembly of claim 7, further including means for securing the proximal end of the shaft to a proximal end of the second shaft.

10. A method of supporting a braidless guide catheter for positioning the catheter within a patient's vascular system, the method comprising:
    providing an elongate shaft including a core having a nonmetallic coating;
    inserting the shaft within the patient's vascular system;
    advancing an elongate tubular member formed of a polymeric layer over the shaft, the shaft being of sufficient outside diameter for continual slidable contact with the tubular member, thereby supporting and guiding the tubular member;
    positioning a distal end of the tubular member within the patient's vascular system.

11. The method of claim 10, further comprising the step of:
    positioning a distal end of the shaft within an ostium of the patient's vascular system.

12. The method of claim 11, further comprising the step of:
    advancing the tubular member over the shaft until a distal end of the tubular member is positioned within the ostium.

13. The method of claim 10, further comprising the step of:
    removing the shaft.

14. A method of supporting a braidless guide catheter for positioning the catheter within a patient's vascular system, the method comprising:
    providing a first elongate tubular member;
    inserting the first elongate tubular member within a second elongate tubular member to form a catheter assembly, wherein the first elongate tubular member is of a sufficient outside diameter for continual slidable contact with the second elongate tubular member, thereby supporting and guiding the second elongate tubular member within the catheter assembly;
    inserting the catheter assembly within a patient's vascular system; and
    positioning a distal end of the catheter assembly within the patient's vascular system.

15. The method of claim 14, further including the step of:
    locking a proximal end of the first tubular member to the proximal end of the second tubular member.

16. The method of claim 14, further including the step of:
    engaging a distal end of the second tubular member in an ostium of a coronary within the vascular system.

17. The method of claim 14, wherein a distal end of the first tubular member extends beyond a distal end of the second tubular member, further comprising the steps of:
    engaging the distal end of the first tubular member within an ostium of a coronary within the vascular system.

18. The method of claim 17, further comprising the steps of:
    tracking the second tubular member over the first tubular member until the distal end of the second tubular member is engaged in the ostium; and
    removing the first tubular member from the patient's vascular system.

19. The method of claim 14, wherein the second tubular member is formed of a polymeric material.

20. The method of claim 14, further including:
    removing the second tubular member from the patient's vascular system.

21. The method of claim 14, wherein the first tubular member is formed of a polymeric material.

* * * * *